United States Patent
Hagg et al.

(10) Patent No.: US 8,623,008 B2
(45) Date of Patent: Jan. 7, 2014

(54) ADAPTER DEVICE

(75) Inventors: Martin Hagg, Wannweil (DE); Uwe Schnitzler, Tübingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 1499 days.

(21) Appl. No.: 11/572,023

(22) PCT Filed: Jul. 14, 2005

(86) PCT No.: PCT/EP2005/007682
§ 371 (c)(1), (2), (4) Date: Jan. 12, 2007

(87) PCT Pub. No.: WO2006/008072
PCT Pub. Date: Jan. 26, 2006

(65) Prior Publication Data
US 2008/0004617 A1 Jan. 3, 2008

(30) Foreign Application Priority Data
Jul. 15, 2004 (DE) .................... 10 2004 034 315
Aug. 27, 2004 (DE) .................... 10 2004 041 623

(51) Int. Cl.
*A61B 18/14* (2006.01)
(52) U.S. Cl.
USPC ............................................. 606/41; 606/45
(58) Field of Classification Search
USPC .................................................. 606/32–50
See application file for complete search history.

(56) References Cited

U.S. PATENT DOCUMENTS

| | | | | |
|---|---|---|---|---|
| 3,799,168 | A | * | 3/1974 | Peters ............................ 606/45 |
| 4,901,719 | A | * | 2/1990 | Trenconsky et al. ............ 606/49 |
| 5,312,401 | A | * | 5/1994 | Newton et al. .................. 606/46 |
| 5,630,812 | A | * | 5/1997 | Ellman et al. ................... 606/41 |
| 5,785,708 | A | * | 7/1998 | Betsill et al. .................... 606/43 |
| 5,814,043 | A | * | 9/1998 | Shapeton ......................... 606/48 |
| 6,361,533 | B1 | | 3/2002 | Morales et al. |
| 2003/0014040 | A1 | | 1/2003 | Shapeton et al. |
| 2003/0073348 | A1 | | 4/2003 | Ries et al. |

FOREIGN PATENT DOCUMENTS

| | | |
|---|---|---|
| DE | 26 39 157 A1 | 3/1978 |
| DE | 3612646 A1 | 4/1987 |

(Continued)

OTHER PUBLICATIONS

Business-Katalog 2004; Dec. 23, Conrad Electronic GmbH, Hirschau, XP0023560454.
ELV Hauptkatalog 2004, Sep. 2003; ELV Elektronik AG, Leer, XP002350455.

*Primary Examiner* — Michael Peffley
(74) *Attorney, Agent, or Firm* — Dickstein Shapiro LLP

(57) ABSTRACT

An adapter is provided for a power connection element between a handle and an electrosurgical instrument to be attached to it. This provides an adapter that makes it possible to reduce organizational effort and costs in the production of electrosurgical instruments with monopolar electrodes. To this end, the adapter includes an insulating portion for adapting an insulating section of the power connection element and an electrically conductive portion for adapting at least one electrically conductive section of the power connection element. The insulating portion and the electrically conductive portion are configured in such a way that the insulating section and the electrically conductive section have their dimensions increased.

17 Claims, 2 Drawing Sheets

(56) References Cited

FOREIGN PATENT DOCUMENTS

| DE | 199 02 642 | A1 | 7/2000 |
|---|---|---|---|
| EP | 0317475 | A | 5/1989 |
| JP | 2001-517974 | A | 10/2001 |
| WO | WO 98/09575 | A1 | 3/1998 |
| WO | 98/36697 | | 8/1998 |
| WO | WO 03/059439 | A2 | 7/2003 |

* cited by examiner

ADAPTER DEVICE

CROSS-REFERENCE TO RELATED APPLICATIONS

This application is a Section 371 of International Application No. PCT/EP2005/007682, filed Jul. 14, 2005, which was published in the German language on Jan. 26, 2006, under International Publication No. WO2006/008072 A3, the disclosure of which is incorporated herein by reference.

BACKGROUND OF THE INVENTION

The invention relates to an adapter for an electrosurgical instrument and in particular for a power connection element located between a handle and an electrosurgical instrument adapted to be fastened to it.

For many years now, electrosurgical instruments have been in use in high-frequency surgery to coagulate or cut biological tissue. In the case of coagulation, a high-frequency current is passed through the tissue under treatment so that it contracts as a result of protein coagulation and dehydration, sealing vessels and making it possible to arrest bleeding. An increase in the current density permits complete separation, i.e. cutting of the tissue.

To perform operations, electrosurgical instruments with monopolar electrodes are used, among other things, in HF surgery. The electrodes, for example ball or loop electrodes, are usually arranged at one distal end of a shank. One proximal end of the shank comprises a power connection element shaped to accommodate a handle so that the electrosurgical instrument can be connected to an HF generator via the handle.

Commercially available electrosurgical instruments with monopolar electrodes have a shank diameter of 2.35 mm or 4.00 mm, and the size of the power connection elements is coordinated to the respective shank diameter. Problems are caused by the fact that instruments with different shank diameters are manufactured on two different production lines and, for example, the single parts needed for production have to be stocked completely. The realization of differing production processes, however, calls for a considerable organizational effort and is costly.

BRIEF SUMMARY OF THE INVENTION

The invention therefore provides an adapter that makes it possible to reduce organizational effort and costs in the production of electrosurgical instruments with monopolar electrodes.

According to the invention there is provided an adapter for a power connection element located between a handle and an electrosurgical instrument adapted to be attached to it that comprises an insulation portion for adapting at least on insulation section of the power connection element and an electrically conductive portion for adapting at least one electrically conductive section of the power connection element. The insulation portion and the electrically conductive portion are configured in such a way that the insulating section and the electrically conductive section may have their dimensions increased.

Hence, in view of the invention, only the electrosurgical instruments with the smaller shank diameter have to be manufactured. With the aid of the adapter, instruments with the larger diameter can be produced using those with the smaller shank diameter so that both types of instruments can be obtained from one production line only. In a first preferred embodiment the insulating portion and/or the electrically conductive portion are essentially configured in a sleeve shape. The portions can then be preferably arranged over the appropriate sections, i.e. over the insulating section and the conductive section of the power connection element in the simplest of ways because the portions only need to be pushed over the electrosurgical instrument. The sleeve-shaped portions can also be manufactured easily and at low cost.

In a further preferred embodiment, the insulating portion envelops at least the insulating section essentially in a form fit. The insulating element is therefore provided with the geometry and thus also the characteristics of the insulating section.

The insulating portion preferably comprises a rotation lock configured particularly as a hexagonal part. The rotation lock is already provided on the insulating section of the power connection element to ensure reliable arresting of the handle. As the insulating portion also features a rotation lock, the handle can be fitted in the usual way and the instrument can be operated in the usual way with the handle.

The electrically conductive portion preferably envelops at least one electrically conductive section essentially in a form fit. The electrically conductive portion is provided with the geometry and the characteristics of the electrically conductive section and the instrument can be operated in the usual way.

In one embodiment the insulating portion is firmly connected to the electrically conductive portion. Hence, the complexity of fitting the adapter device to the electrosurgical element can be minimized because the adapter device can be fitted onto the electrosurgical instrument in one single operation.

The insulating portion and the electrically conductive portion are preferably capable of being connected to one another. If it is intended to produce the insulating portion and the electrically conductive portion as independent components, these can be replaced easily, for example if they have been damaged. However, a screwable connection ensures a reliable connection when the portions are fitted together.

In a further embodiment, the insulating portion and the electrically conductive portion can be connected to one another by means of a plug connection. The plug connection ensure particularly easy assembly and disassembly of the components so as to ensure fast and easy replacement of one single component.

The portions are preferably configured so that, when fitted, they are at least at such a distance from the sections of the power connection element to rule out tilting during assembly. End welding of the electrically conductive section and electrically conductive portion then ensures reliable arresting of the adapter and establishes electrical contact.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

The invention will now be described by way of example with reference to the accompanying figures.

In the drawings:

FIG. 1 is an exploded side view of an electrosurgical instrument an adapter according to the invention.

FIG. 2 is a side view of the electrosurgical instrument shown in FIG. 1 with the adapter fitted thereto.

FIG. 3 is an exploded side view to an enlarged scale of a proximal end of the electrosurgical instrument shown in FIG. 1.

FIG. 4 is a side view to an enlarged scale of the proximal end of the electrosurgical instrument shown in FIG. 1, with the adapter fitted to the electrosurgical instrument shown in section.

DETAILED DESCRIPTION OF THE INVENTION

In the following description, the same reference numbers are used to denote identical parts and those that have an identical effect.

Figure 1:
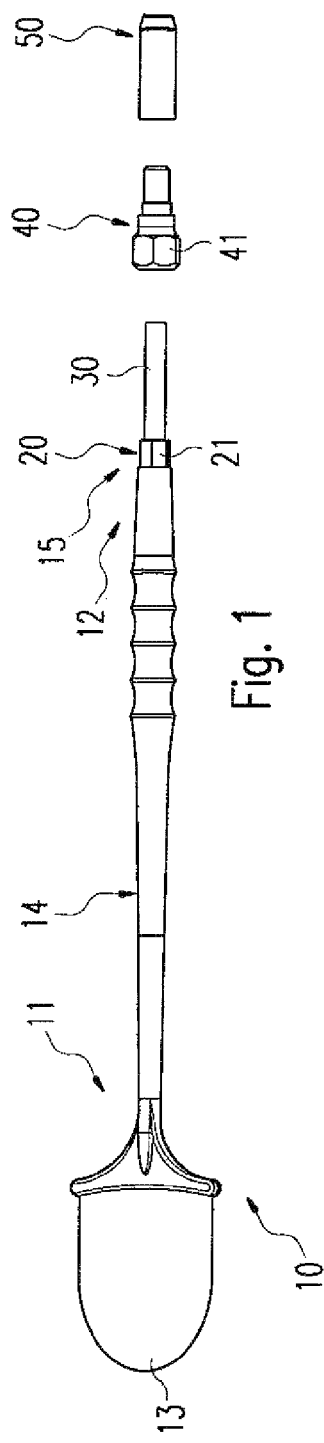

FIG. 1 shows an electrosurgical instrument 10 in an embodiment whereby the instrument 10 comprises an electrode 13 at one distal end. The electrode 13 is configured on a shank 14 of the electrosurgical instrument 10. A power connection element 15 is provided on one proximal end 12 of the electrosurgical instrument 10. The power connection element 15 consists of an insulating section 20 and an electrically conductive section 30. The insulating section 20 comprises a hexagonal part 21.

Commercially available electrosurgical instruments with monopolar electrodes are configured with a shank diameter of 2.35 mm or 4.00 mm. In FIG. 1, the electrosurgical instrument 10 is shown with a shank diameter of 2.35 mm. The power connection element 15 is designed accordingly. To provide the illustrated instrument 10 with a power connection element that is designed according to a shank diameter of 4.00 mm, an insulating element 40 and an electrically conductive element 50 can be pushed over the proximal end 12 of the electrosurgical instrument 10 and thus over the power connection element 15. The insulating element 40 and the electrically conductive element 50 are shown in their non-assembled stated in the figure.

In the fitted state, the insulating element 40 envelops the insulating section 20 and an area of the electrically conductive section 30. Just like the insulating section 20, the insulating element 40 comprises a hexagonal part 41 on a first end of the insulating section 40. On later fitting of a handle (not shown), the hexagonal part 41 serves as a rotation lock for the handle. This ensures that the handle is reliably fastened on the electrosurgical instrument 10 and the operating surgeon can reliably guide the electrosurgical instrument 10 during treatment. In this embodiment, the insulating element 40 and the electrically conductive element 50 are sleeve-shaped so they can be pushed very easily over the power connection element 15. According to this embodiment, the insulating element 40 and the electrically conductive element 50 are capable of being connected to one another by plugging. This ensures easy assembly and disassembly of the elements.

As an alternative, it is possible to connect the insulating element and the electrically conductive to one another by means of a screwed connection. The screwed connection ensures a reliable connection when the elements are fitted together. If the two elements are firmly connected to one another, the complexity of fitting the adapter device to the electrosurgical element can be minimized because the adapter device can be fitted onto the electrosurgical instrument in one single operation.

Figure 2:
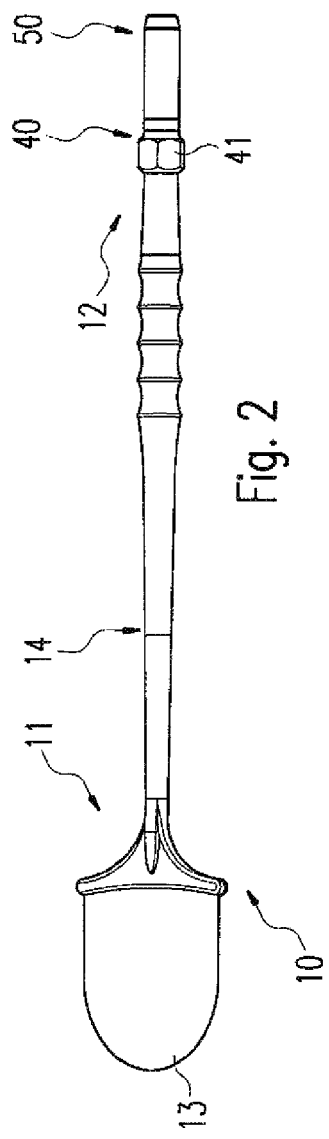

FIG. 2 shows the electrosurgical element 10 from FIG. 1, whereby here the power connection element is already provided with the insulating element 40 and the electrically conductive element 50.

Figure 3:
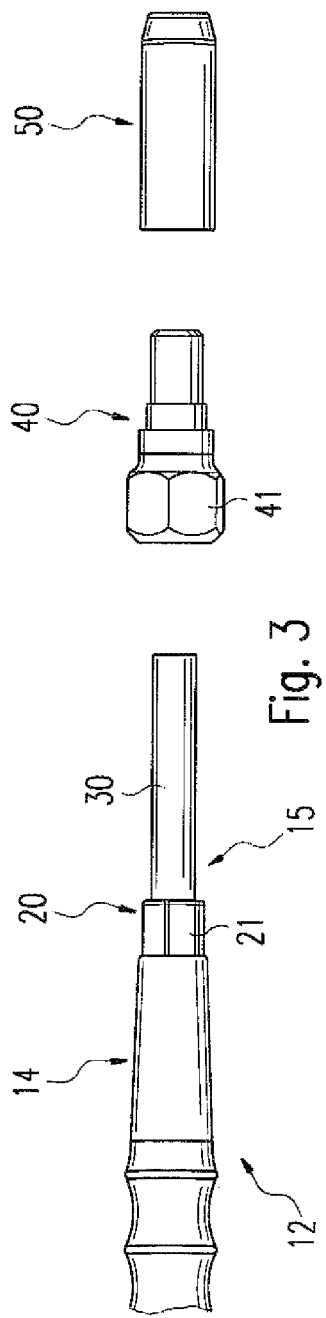

FIG. 3 shows the proximal end 12 of the electrosurgical instrument according to FIG. 1, and this is an enlarged illustration in comparison with FIG. 1.

Figure 4:
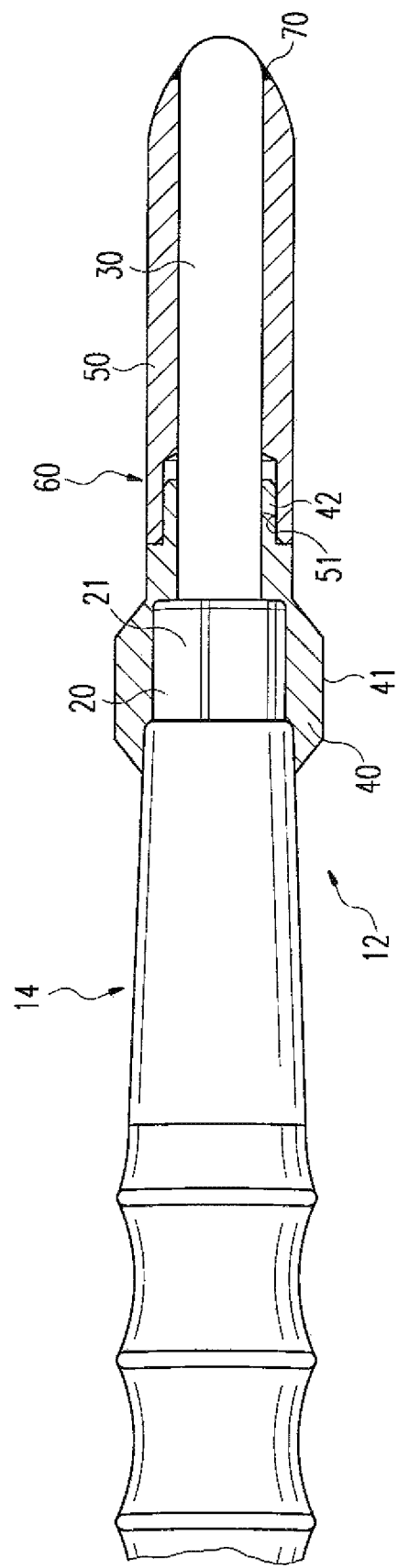

FIG. 4 shows the proximal end 12 of the electrosurgical instrument according to FIG. 1. The adapter device fitted to the electrosurgical instrument is shown in a section. The insulating element 40 or the electrically conductive element 50 is pushed over the insulating section 20 or an electrically conductive section 30. As can be seen in the figure, the insulating element 40 and the electrically conductive element 50 are connected to one another by means of a plug connector 60. To this end, at one end pointing towards the insulating element 40 the electrically conductive element 50 comprises a rotation-symmetrical recess 51, into which an appendage 42 of the insulating element 40 can be pushed. As can be seen in the figure, the insulating element 40 and the electrically conductive element 50 envelop the insulating section 20 or the electrically conductive section 30 essentially in a form fit. The insulating element 40 or envelops an area of the electrically conductive section 30. The sleeve-shaped insulating element 40 is configured in an area enveloping the insulating section 20 in such a way that the hexagonal part 21 of the insulating section 20 can be accommodated in the insulating element 40 and, in this embodiment, once again comprises the hexagonal part 41 on an outer circumference. The hexagonal parts are intended as rotation locks so as to ensure fitting of a handle (not shown) on the electrosurgical instrument without subsequent rotation of the handle being enabled. To ensure a reliable connection between the sections and the elements and electrical contact between the electrically conductive section 30 and the electrically conductive element 50, the electrically conductive element 50 is welded to the electrically conductive section 30 at the end, i.e. by means of a weld 70 at an end opposite the plug connector 60.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An adapter for a power connection element located between a handle and an electrosurgical instrument adapted to be fastened to it, the electrosurgical instrument including a shank, the power connection element being designed in accordance with a diameter of the shank of the electrosurgical instrument, and the handle being adapted to accommodate a power connection element designed in accordance with a larger shank diameter than the diameter of the shank of the electrosurgical instrument, the adapter comprising:

an insulating portion adapted for fitment to at least one insulating section of the power connection element; and an electrically conductive portion adapted for fitment to at least one electrically conductive section of the power connection element, wherein the insulating portion and the electrically conductive portion are detachable from each other and the insulating portion is adapted to envelope the at least one insulating section and the electrically conductive portion is adapted to envelope the at least one electrically conductive section, thereby comprising geometry and characteristics of the insulating section and electrically conductive section, respectively, wherein the insulating portion and the electrically conductive portion are configured such that, in use, the adapter causes dimensions of the at least one insulating section and the at least one electrically conductive section of the power connection element to be increased by the adapter, thereby forming the power connection element designed in accordance with the larger shank diameter for accommodation by the handle, and wherein the electrically conductive portion comprises a rotation-symmetrical recess at one end thereof, into which an appendage of the insulating portion can be pushed when attached to the electrically conductive portion.

2. The adapter according to claim 1, wherein at least one of the insulating portion and the electrically conductive portion has a sleeve-shaped form.

3. The adapter according to claim 1, wherein the insulating portion is adapted in use to envelop at least the insulating section in a form fit.

4. The adapter according to claim 1, wherein the insulating portion comprises a rotation lock.

5. The adapter according to claim 1, wherein the electrically conductive portion is adapted in use to envelop at least the electrically conductive section in a form fit.

6. The adapter according to claim 1, wherein the insulating portion and the electrically conductive portion are permanently connected to one another.

7. The adapter according to claim 1, wherein the insulating portion and the electrically conductive portion are connectable to one another via a screwed connection.

8. The adapter according to claim 1, wherein the insulating portion and the electrically conductive portion are connectable to one another via a plug connection.

9. A system comprising an electrosurgical instrument and an adapter for a power connection between a handle and a power connection element of the electrosurgical instrument adapted to be fastened to it, the electrosurgical instrument including a shank, the power connection element being designed in accordance with a diameter of the shank of the electrosurgical instrument, and the handle being adapted to accommodate a power connection element designed in accordance with a larger shank diameter than the diameter of the shank of the electrosurgical instrument, the adapter comprising:

an insulating portion adapted for fitment to at least one insulating section of the power connection element; and an electrically conductive portion adapted for fitment to at least one electrically conductive section of the power connection element, wherein the insulating portion and the electrically conductive portion are detachable from each other and the insulating portion is adapted to envelope the at least one insulating section and the electrically conductive portion is adapted to envelope the at least one electrically conductive section, thereby comprising geometry and characteristics of the insulating section and electrically conductive section, respectively, wherein the insulating portion and the electrically conductive portion are configured such that, in use, the adapter causes dimensions of the at least one insulating section and the at least one electrically conductive section of the power connection element to be increased by the adapter, thereby forming the power connection element designed in accordance with the larger shank diameter for accommodation by the handle, and wherein the electrically conductive portion comprises a rotation-symmetrical recess at one end thereof, into which an appendage of the insulating portion can be pushed when attached to the electrically conductive portion.

10. The system according to claim 9, further comprising the handle.

11. The system according to claim 9, wherein at least one of the insulating portion and the electrically conductive portion has a sleeve-shaped form.

12. The system according to claim 9, wherein the insulating portion is adapted in use to envelop at least the insulating section in a form fit.

13. The system according to claim 9, wherein the insulating portion comprises a rotation lock.

14. The system according to claim 9, wherein the electrically conductive portion is adapted in use to envelop at least the electrically conductive section in a form fit.

15. The system according to claim 9, wherein the insulating portion and the electrically conductive portion are permanently connected to one another.

16. The system according to claim 9, wherein the insulating portion and the electrically conductive portion are connectable to one another via a screwed connection.

17. The system according to claim 9, wherein the insulating portion and the electrically conductive portion are connectable to one another via a plug connection.

* * * * *

UNITED STATES PATENT AND TRADEMARK OFFICE
CERTIFICATE OF CORRECTION

PATENT NO.        : 8,623,008 B2  
APPLICATION NO.   : 11/572023  
DATED             : January 7, 2014  
INVENTOR(S)       : Hagg et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1602 days.

Signed and Sealed this
Twenty-second Day of September, 2015

Michelle K. Lee
*Director of the United States Patent and Trademark Office*